(12) United States Patent
Brioschi et al.

(10) Patent No.: US 7,274,715 B2
(45) Date of Patent: Sep. 25, 2007

(54) METHOD AND APPARATUS FOR AUTOMATIC DELAY COMPENSATION IN SPACE DIVERSITY RADIO TRANSMISSIONS

(75) Inventors: Massimo Brioschi, Monza (IT); Roberto Pellizzoni, Cantu' (IT); Roberto Valtolina, Trezzo sull' Adda (IT); Arnaldo Spalvieri, Milan (IT)

(73) Assignee: Alcatel, Paris (FR)

( * ) Notice: Subject to any disclaimer, the term of this patent is extended or adjusted under 35 U.S.C. 154(b) by 830 days.

(21) Appl. No.: 09/833,666

(22) Filed: Apr. 13, 2001

(65) Prior Publication Data

US 2002/0048261 A1 Apr. 25, 2002

(30) Foreign Application Priority Data

Apr. 14, 2000 (IT) .......................... MI2000A0833

(51) Int. Cl.
*H04J 3/06* (2006.01)
(52) U.S. Cl. ........................ 370/516; 370/517; 370/519
(58) Field of Classification Search ................ 370/516, 370/517, 519; 375/229, 234, 349
See application file for complete search history.

(56) References Cited

U.S. PATENT DOCUMENTS

| | | | |
|---|---|---|---|
| 4,278,978 A | | 7/1981 | Frosch et al. |
| 5,127,025 A | * | 6/1992 | Okanoue .................... 375/347 |
| 5,621,769 A | * | 4/1997 | Wan et al. .................... 375/347 |
| 5,646,958 A | * | 7/1997 | Tsujimoto .................... 375/233 |
| 5,805,983 A | * | 9/1998 | Naidu et al. ............. 455/67.16 |
| 5,907,303 A | | 5/1999 | Yukitomo et al. |
| 5,926,502 A | | 7/1999 | Schilling |
| 6,115,419 A | * | 9/2000 | Meehan ....................... 375/233 |
| 6,353,629 B1 | * | 3/2002 | Pal .............................. 375/222 |

OTHER PUBLICATIONS

"Data Communications Principles" by R. Gitlin, J. Hayes, S. Weinstein, et. Plenum Press, New York, 1992, paragraph 7.4.4, pp. 493-495.
H. Wilck; "A Signal Combiner for Antenna Arraying" JPL Deep Space Network Progress Report 42-25, 'Online!, Feb. 15, 1997, pp. 111-117, XP002347959 Pasadena, California.

* cited by examiner

*Primary Examiner*—Wing Chan
*Assistant Examiner*—Richard Chang
(74) *Attorney, Agent, or Firm*—Sughrue Mion, PLLC

(57) ABSTRACT

A method and apparatus is described for the automatic delay compensation in space diversity radio transmissions. The method includes the steps of: a) receiving a first analog signal and a second analog signal, a possible delay being between the first and second signals; b) sampling the first and the second analog signals to obtain a first digital signal and a second digital signal, respectively; c) sending the digital signals to respective equalizers, and the steps of d) digitally delaying one of the first digital signal and the second digital signal by a period equal to an integral multiple of the sampling period, and e) recovering, at the equalization phase, the residual difference between the imposed delay and the actual one.

11 Claims, 3 Drawing Sheets

METHOD AND APPARATUS FOR AUTOMATIC DELAY COMPENSATION IN SPACE DIVERSITY RADIO TRANSMISSIONS

BACKGROUND OF THE INVENTION

1. Field of the Invention

The present invention relates to the field of radio transmissions and in particular it relates to the space diversity systems. Still more in particular, it concerns a method and an apparatus for compensating, in an automatic and digital manner, the relative delay between the two (or more) signals received simultaneously.

2. Description of the Prior Art

In a high-capacity radio transmission system the channel distorting effects are well known, mainly due to the multipath phenomenon: the receiving antenna can in fact receive, along with the wished signal, a delayed replica thereof, caused by the reflection of the transmitted signal from tropospheric layers having unusual physical characteristics or by the reflection from orographic obstacles. Such a corruptive effect is known in the leterature as selective fading. Under exceptionally unfavourable conditions the fading can even result in the radio system to be out-of-order, since the received signal becomes no longer intelligible.

A first, possible and widely used in practice, countermeasure is represented by the adaption of an adaptive equalizer inside the demodulation apparatus. This solution, sometimes, may be not enough in the case of radio spans extraordinarily long or installed under exceptionally unfavourable geographic conditions.

Another possible alternative consists in providing a space diversity system, based upon the transmission of a signal which is received simultaneously by two or more different antennas (hereafter, two antennas will be considered by way of a non limiting example). The operating philosophy of the space diversity system consists exactly in sending the same information to the receiver by means of two distinct signals (one will be called "main" and the other will be called "diversity"). The effectiveness of this method depends on the fact that if the antennas are sufficiently spaced out in height, the received signals can be deemed uncorrelated and hence it is extremely unlikely that both signals exhibit the same quality at the same instant.

Two main methods for processing the pairs of received signals are known: switching and combination. Switching is based on the selection, theoretically at every instant, of the best of the two signals through a suitable criterion (typically the BER or Bit Error Rate).

An approach deemed more effective consists in processing the two diversity signals by properly combining them. The procedure often used in this case is the one illustrated in FIG. 1, in which the two signals, main and diversity, suitably sampled, are the inputs of two FSEs (Fractionally Spaced Equalizers) whose output is summed and represents the result of the combination.

However, because of the different positioning height of the two antennas at the receiving tower, of the different length of the waveguides or in any case of the various connection cables, the main and diversity signals may reach the samplers of FIG. 1 delayed one to each other. In order to realize the combination in an effective manner it is necessary to compensate for such a delay. Generally, once the delay has been measured by means of proper instruments, it is compensated during the installation of the radio link by adding to one of the two signals a cable length such that the transit time is equal to the delay to be compensated of by means of proper analog delay cells suitably adjustable.

Unfortunately, this solution has the drawback of entailing a high cost and of the need to carry out the calibration on the field (thus requiring long times to reach the antennas).

SUMMARY OF THE INVENTION

The main object of the present invention is therefore to provide a method and an apparatus for compensating the relative delay between the two paths.

The main object is providing a method of compensating a possible delay between two or more radio transmission paths in space diversity radio transmissions, wherein the method comprises the steps of: receiving a first analog signal; receiving at least a further analog signal; sampling said first and said at least a further analog signals, to obtain a first digital signal and at least a further digital signal, respectively, a possible delay being present between the first and the at least a further digital signals; and sending said digital signals to respective equalizers, wherein the method comprises the further step of delaying in a digital manner one of said first digital signal and said at least a further digital signal by a period equal to an integer multiple of the sampling period, and possibly the step of recovering, at the equalization step, the difference between the imposed delay and the real one.

A further object of the present invention is providing an apparatus for compensating the delay between two or more radio transmission lines in space diversity radio transmissions, wherein the apparatus comprises: means for receiving a first analog signal; means for receiving at least a further analog signal; means for sampling the first and the at least a further analog signals to obtain, a first digital signal and at least a further digital signal, respectively, a possible delay being present between the first and the at least a further digital signals; and equalizers receiving said digital signals at the input, wherein the apparatus further comprises means for delaying in a digital manner one of said first digital signal and said at least a further digital signal by a period equal to an integer multiple of the sampling period, and equalizer means capable of restoring the difference between the imposed delay and the effective one.

In accordance with the present invention, the compensation is carried out in a digital and automatic manner.

The invention will become clear in view of the following detailed description, given by way of a mere non limiting example to be read with reference to the appended drawing figures.

BEST MODE FOR CARRYING OUT THE INVENTION

Figure 1:
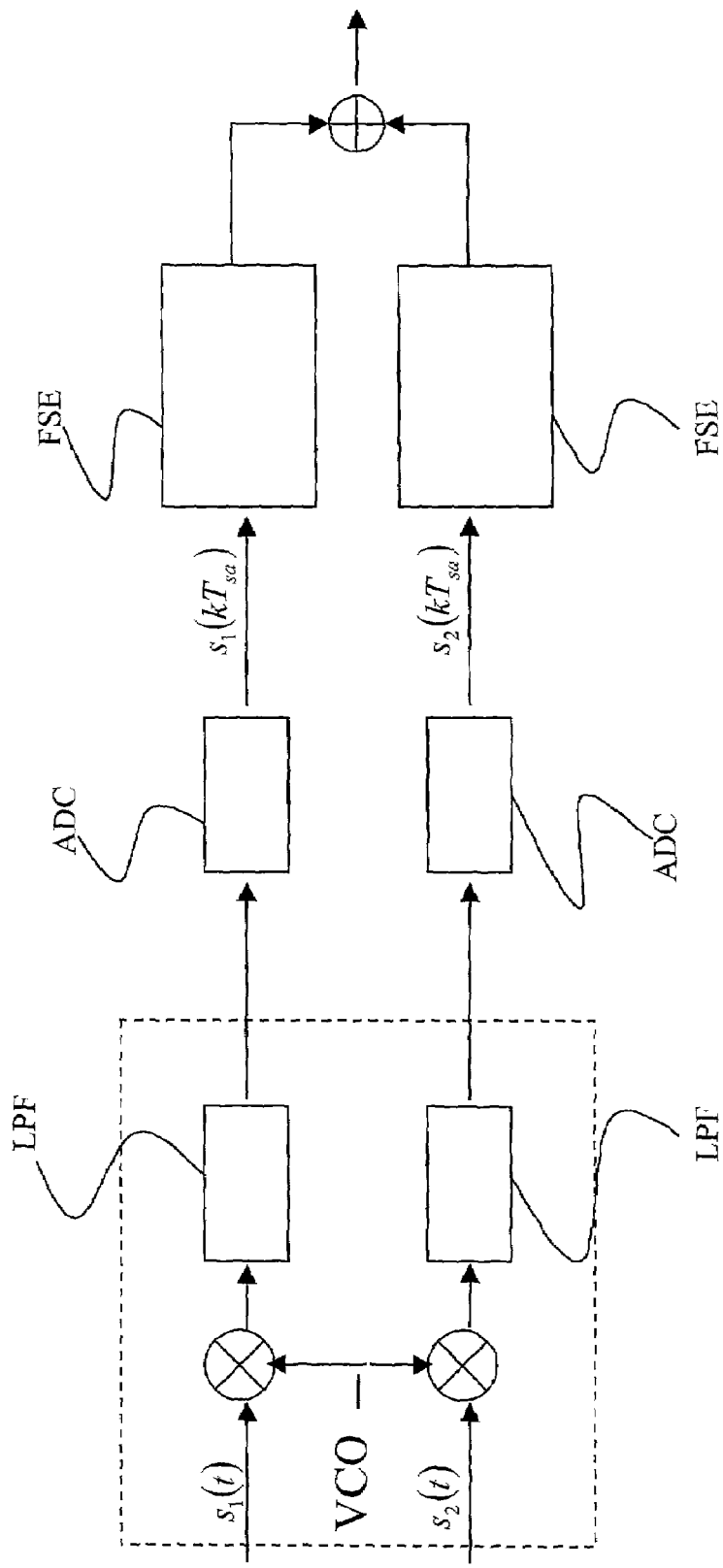
FIG. 1 is a basic diagram of a baseband combiner according to the prior art, parts related to the base-band down-conversion and to the analog signal sampling by means of analog to digital converters being indicated.
Figure 2:
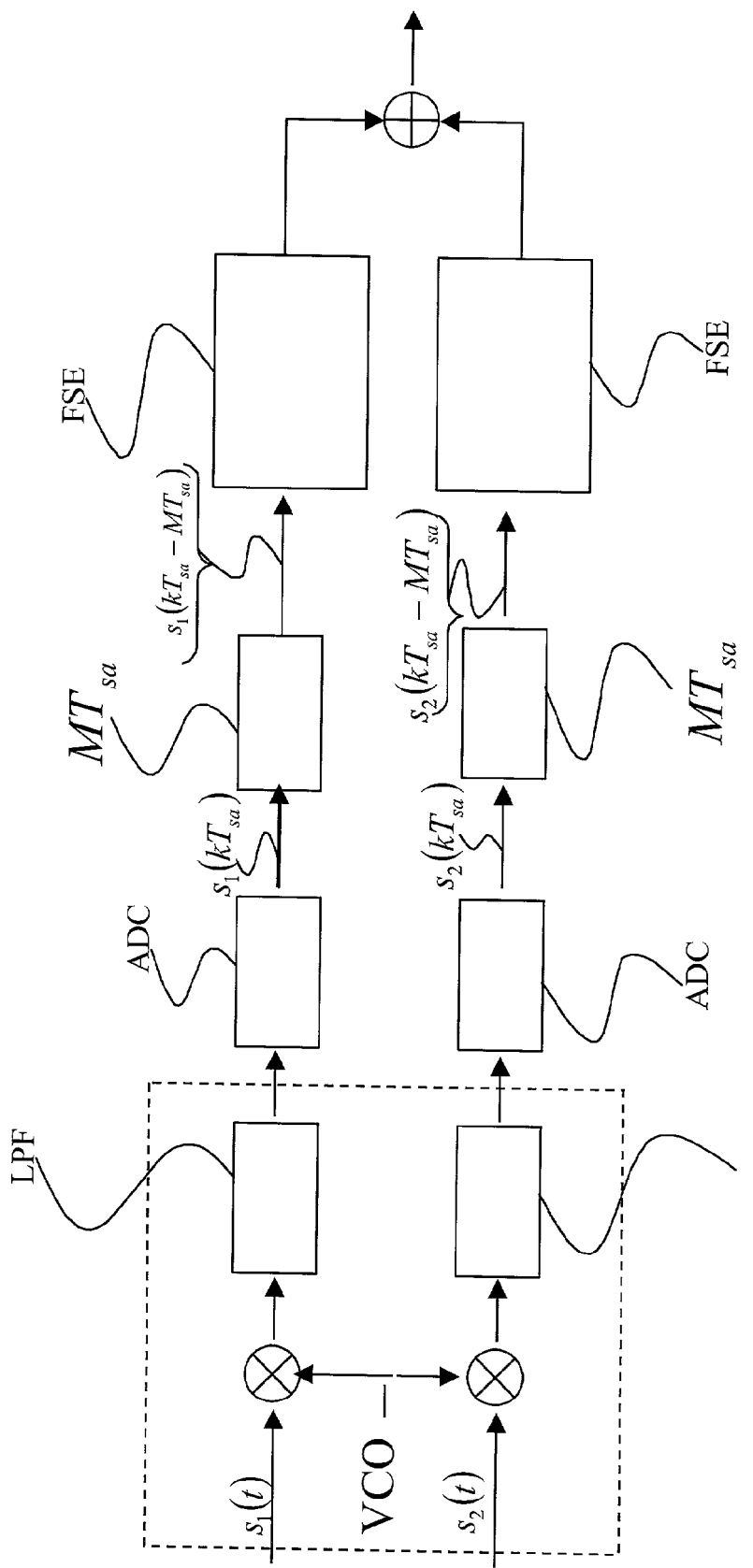
FIG. 2 is a basic diagram of a base-band combiner with the two delayed paths.

As said above, an apparatus according to the prior art is illustrated in FIG. 1, which apparatus processes the two signals and combines them suitably. The two signals, main and diversity ($S_1(t)$, $S_2(t)$) are entered into a voltage controlled oscillator (VCO) and are low-pass filtered (LPF); each of them is then passed through an analog to digital converter (ADC) for sampling and through a fractionally spaced equalizer (FSE). The outputs from the equalizers are then summed and substantially represent the result of the combination. The dashed-line square in FIG. 1 (and similarly in FIG. 2) represents the analog portion of the device).

In order to implement the combination in an effective manner it is, on the other hand, necessary to compensate for the delay with which the signals reach the samplers. Consider for instance two signals entering the demodulator and coming from the main antenna (signal 1) and from the diversity antenna (signal 2), respectively. If signal 1 is $\tau$ seconds late after signal 2, in order to be able to realize the combination in an effective manner, it is necessary to delay, in principle, the signal 2 by $\tau$ seconds.

Let $s_1(t)$ and $s_2(t)$ be the two analog signals at the input of the demodulator, namely:

$$s_1(t) = \sum_{k=-\infty}^{+\infty} a_k g_1(t - kT - \tau) \text{ and } s_2(t) = \sum_{k=-\infty}^{+\infty} a_k g_2(t - kT)$$

$a_k$ being the transmitted symbol, T being the signalling interval and $g_1(t)$ and $g_2(t)$ being the pulse responses comprising the transmit and receive filtering chain and the pulse response of the channel as "viewed" from the main antenna and from the diversity antenna, respectively.

Let $s_1(KT_{sa})$ and $s_2(KT_{sa})$ the main and diversity signals sampled with period $T_{sa}$ by the analog to digital converter (ADC). So it is possible to digitally delay the signal 2 by a period equal to integer multiples of $T_{sa}$, namely such that $M \cdot T_{sa}$, M being an integer, be as much as possible an approximation of the delay $\tau$ (see FIG. 2). The difference $|MT_{sa} - \tau|$, however being still less than $T_{sa}/2$, will be recovered by the equalizers (FSE) by virtue of their interpolation capabilities (see, e.g., the publication "Data Communications Principles" by R. Gitlin, J. Hayes, S. Weinstein, ed. Plenum Press, New York, 1992, paragraph 7.4.4, pages 493 to 495).

The algorithm which is the subject-matter of the present invention seeks to determine, in an automatic manner, the value of M (without knowing a priori if signal 1 is late after signal 2 or vice versa), by operating in the way that will be described below with reference to FIG. 3.

First, several delayed replicas of both signal 1 and of signal 2, are obtained, namely signals of the following type are obtained:

$$r_{1j}(kT_{sa}) = s_1(kT_{sa} - jT_{sa}) \text{ and } r_{2i}(kT_{sa}) = s_2(kT_{sa} - iT_{sa})$$

with $0 \leq j \leq N_1$ and $0 \leq i \leq N_2$, $N_1 T_{sa}$ being the maximum assumable delay of signal 1 with respect to signal 2 and, similarly, $N_2 T_{sa}$ being the maximum assumable delay of signal 2 with respect to signal 1.

Note that in general it may happen that $N_1 \neq N_2$.

Figure 3:
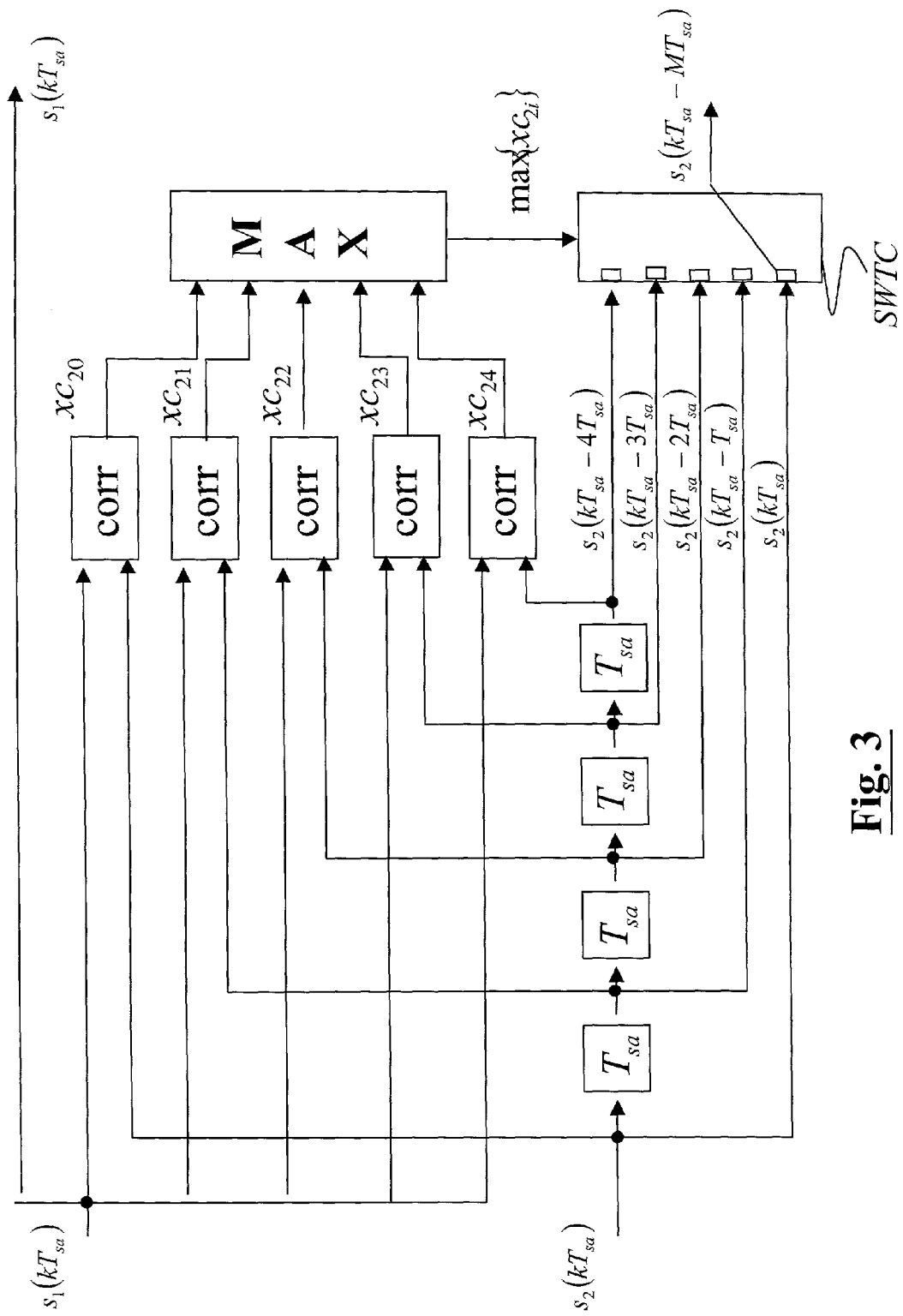
FIG. 3 schematically shows the compensation apparatus according to the present invention.

In FIG. 3, only by way of example and not of limitation, it has been set $N_1 = 0$ and $N_2 = 4$ for simplicity.

Thereafter the various cross-correlations are calculated $$xc_{1j} = E\{s_1(kT_{sa} - \tau - jT_{sa}) \cdot s_2^*(kT_{sa})\} = \qquad (1)$$
$$= E\left\{\sum_m \sum_n a_n a_m * g_2 * (kT_{sa} - mT) g_1(kT_{sa} - nT - \tau - jT_{sa})\right\}$$
with $0 \leq j \leq N_1$ $$xc_{2i} = E\{s_1^*(kT_{sa} - \tau) \cdot s_2(kT_{sa} - iT_{sa})\} = \qquad (2)$$
$$= E\left\{\sum_m \sum_n a_m a_n * g_1^*(kT_{sa} - nT - \tau) g_2(kT_{sa} - mT - iT_{sa})\right\}$$
with $0 \leq i \leq N_2$ where * denotes the complex conjugate operation and $E\{\cdot\}$ the time-average operation.

Then, the maximum value between $xc_{1j}$ and $xc_{2i}$ is determined as i and j are varied, normally will be $$M = \max_{i,j}(|xc_{1j}|^p, |xc_{2i}|^p).$$

p being a positive integer higher than 0.

In fact, considering that $g_1(t) \cong g_2(t)$ (indeed the installation occurs in the absence-of-fading condition, and hence the channel which is viewed from the two antennas is very similar) and that the autocorrelation of $g_1(t)$ or $g_2(t)$ is at its maximum for t=0 (about the way the filterings are normally constituted), it is clear that in the case in question, the modulus of the cross-correlation best approximating $E\{s_1(t)s_2^*(t-\tau)\}$ will be a maximum.

Either signal 1 or signal 2 of $MT_{sa}$ is delayed, depending on whether the correlation is of type $xc_{1j}$ or of type $xc_{2i}$.

Clearly, the cross-correlations xc are complex numbers; in order to calculate the maximum thereof, their modulus raised to "p", should be calculated, p being a positive integer, usually equal to 2 for convenience.

In FIG. 3 a possible circuit implementation is shown wherein the switching circuit (SWTC), according to the information which are received from the computation of the maximum, selects the proper delay to be inserted (in this case on path 2); "corr" denotes the computation of the cross-correlation, as indicated above.

Although in FIG. 3 it has been set $N_1 = 0$ and $N_2 = 4$ for simplicity, any other combination of $N_1$ and $N_2$ is possible and FIG. 3 would assume a correspondingly different aspect.

In practice, however, the device according to the invention would operate assuming first j=0 and making i change from 1 to $N_2$, afterwards assuming i=0 and making j change from 1 to $N_1$ until the value of M is found (as it is apparent from (1) and (2).

It is apparent that the present invention can be embodied in the form of a circuit or a computer software program. The scope of the present patent application therefore covers also such a computer software program and to the computer into which such program is stored and runs.

There have thus been shown and described a novel method and a novel apparatus which fulfill all the objects and advantages sought therefor. Many changes, modifications, variations and other uses and applications of the subject invention will, however, become apparent to those skilled in the art after considering the specification and the accompanying drawings which disclose preferred embodiments thereof. All such changes, modifications, variations and other uses and applications which do not depart from the spirit and scope of the invention are deemed to be covered by the invention which is limited only by the claims which follow.

What is claimed is:

1. A method of compensating for a possible delay between two or more radio transmission paths in space diversity radio transmissions, said method comprises:
receiving a first analog signal;
receiving at least one second analog signal;
sampling said first analog signal and said at least one second analog signal to obtain a first digital signal and at least one second digital signal, respectively, a possible delay being present between the first digital signal and the at least one second digital signal; and
sending said digital signals to respective equalizers;
delaying, in a digital manner, one of said first and second digital signals relative to the other by a period equal to an integer multiple of the sampling period, said delaying comprising automatically calculating a value of said integer multiple, and optionally
recovering, at equalization, the difference between the imposed delay and the real delay.

2. A method according to claim 1, wherein delaying comprises calculating the value of the integer multiple, wherein calculating the integer multiple comprises:
realizing delayed replicas $r_{1j}(kT_{sa})=s_1(kT_{sa}-jT_{sa})$ and $r_{2i}(kT_{sa})=s_2(kT_{sa}-iT_{sa})$ of said first and said at least second digital signals, with $0 \leq j \leq N_1$ and $0 \leq i \leq N_2$, $N_1 T_{sa}$ being the maximum assumable delay of the first signal with respect to the at least one second signal and $N_2 T_{sa}$ being the maximum assumable delay of the at least one second signal with respect to the first signal;
calculating cross-correlations $$xc_{1j}=E\left\{\sum_m \sum_n a_n a_m * g_2 *(kT_{sa}-mT)g_1(kT_{sa}-nT-\tau-jT_{sa})\right\}$$

with $0 \leq j \leq N_1$, $$xc_{2i}=E\left\{\sum_m \sum_n a_m a_n * g_1^*(kT_{sa}-nT-\tau)g_2(kT_{sa}-mT-iT_{sa})\right\}$$

with $0 \leq i \leq N_2$, between the various delayed replicated signals, where * denotes the complex conjugate operation and $E\{\cdot\}$ the time average operation; and
deriving the maximum value of said cross-correlations as i and j vary, namely $$M = \max_{i,j}(|xc_{1j}|^p, |xc_{2i}|^p)$$

said maximum value corresponding to the value of the integer multiple.

3. A method according to claim 2, wherein the method further comprises selecting the delayed replica to be sent to said equalizers as a function of the information related to the maximum of the calculated cross-correlations.

4. An apparatus for compensating a delay between two or more radio transmission lines in space diversity radio transmissions, said apparatus comprising:
means for receiving a first analog signal;
means for receiving at least one second analog signal;
means for sampling the first analog signal and the at least one second analog signal to obtain a first digital signal and at least one second digital signal, respectively, a delay being possibly present between the first digital signal and the at least one second digital signal; and
equalizers receiving said digital signals at their respective inputs;
means for delaying, in a digital manner, one of said first and second digital signals relative to the other by a period equal to an integer multiple of the sampling period, said delaying comprising automatically calculating a value of said integer multiple, and
equalizer means capable of restoring the difference between an imposed delay and the real delay.

5. An apparatus according to claim 4, wherein said delay means comprise means for calculating the value of the integer multiple, wherein said calculation means comprise:
means for realizing delayed replicas $r_{1j}(kT_{sa})=s_1(kT_{sa}-jT_{sa})$ and $r_{2i}(kT_{sa})=s_2(kT_{sa}-iT_{sa})$ of said first and said at least one second digital signals, with $0 \leq j \leq N_1$ and $0 \leq i \leq N_2$, $N_1 T_{sa}$ being the maximum assumable delay of the first signal with respect to the at least one second signal and $N_2 T_{sa}$ being the maximum assumable delay of the at least one second signal with respect to the first signal;
means for calculating cross-correlations $$xc_{1j}=E\left\{\sum_m \sum_n a_n a_m * g_2 *(kT_{sa}-mT)g_1(kT_{sa}-nT-\tau-jT_{sa})\right\}$$

with $0 \leq j \leq N_1$, $$xc_{2i}=E\left\{\sum_m \sum_n a_m a_n * g_1^*(kT_{sa}-nT-\tau)g_2(kT_{sa}-mT-iT_{sa})\right\}$$

with $0 \leq i \leq N_2$, between the various delayed replicated signals, where * denotes the complex conjugate operation and $E\{\cdot\}$ the time average operation; and
means for deriving a maximum value of said cross-correlations as i and j vary, namely $$M = \max_{i,j}(|xc_{1j}|^p, |xc_{2i}|^p),$$

said maximum value corresponding to the value of the integer multiple.

6. An apparatus according to claim 5, further comprising switching means for selecting a proper delayed replica to be sent to said equalizer means as a function of information related to the maximum of the cross-correlations calculated.

7. A computer program comprising computer program code means adapted to perform all the steps of claim 1 when said program is run on a computer.

8. A computer-readable medium having a program recorded thereon, said computer-readable medium comprising computer program code means adapted to perform all the steps of claim 1 when said program is run on a computer.

9. An apparatus for compensating a delay between two or more radio transmission lines in space diversity radio transmissions, said apparatus comprising:
a first receiver that receives a first analog signal;
a second receiver that receives at least one second analog signal;

a sampling circuit that samples the first analog signal and the at least one second analog signal to obtain a first digital signal and at least one second digital signal, respectively, a delay being possibly present between the first digital signal and the at least one second digital signal;

equalizers that receive said digital signals at their respective inputs;

a digital delay circuit that digitally delays one of said first and second digital signals relative to the other by a period equal to an integer multiple of the sampling period, said delaying comprising automatically calculating a value of said integer multiple, and a restoring equalizer that restores the difference between an imposed delay and the real delay.

10. An apparatus according to claim 9, wherein said digital delay circuit comprises a calculation circuit for calculating the value of the integer multiple, wherein said calculation circuit:

a delay circuit that realizes delayed replicas $r_{1j}(kT_{sa})=s_1(kT_{sa}-jT_{sa})$ and $r_{2i}(kT_{sa})=s_2(kT_{sa}-iT_{sa})$ of said first and said at least one second digital signals, with $0 \leq j \leq N_1$ and $0 \leq i \leq N_2$, $N_1T_{sa}$ being the maximum assumable delay of the first signal with respect to the at least one second signal and $N_2T_{sa}$ being the maximum assumable delay of the at least one second signal with respect to the first signal;

a correlation circuit that calculates cross-correlations $$xc_{1j} = E\left\{\sum_m \sum_n a_n a_m * g_2 * (kT_{sa} - mT)g_1(kT_{sa} - nT - \tau - jT_{sa})\right\}$$

with $0 \leq j \leq N_1$, $$xc_{2i} = E\left\{\sum_m \sum_n a_m a_n * g_1 * (kT_{sa} - nT - \tau)g_2(kT_{sa} - mT - iT_{sa})\right\}$$

with $0 \leq i \leq N_2$ between the various delayed replicated signals, where * denotes the complex conjugate operation and $E\{\cdot\}$ the time average operation; and a maximum value circuit derives a maximum value of said cross-correlations as i and j vary, namely $$M = \max_{i,j}(|xc_{1j}|^P, |xc_{2i}|^P),$$

said maximum value corresponding to the value of the integer multiple.

11. An apparatus according to claim 10, further comprising a switch for selecting a proper delayed replica to be sent to said restoring equalizer as a function of information related to the maximum of the cross-correlations calculated.

* * * * *